(12) United States Patent
Elizondo et al.

(10) Patent No.: US 8,480,731 B2
(45) Date of Patent: Jul. 9, 2013

(54) TOOL FOR IMPLANTATION OF REPLACEMENT HEART VALVE

(75) Inventors: David Elizondo, Champlin, MN (US); Larry Peterson, Maple Grove, MN (US); Yang Thai, Brooklyn Park, MN (US); Malewicz M. Andrzej, Minneapolis, MN (US)

(73) Assignee: Medtronic ATS Medical, Inc., Minneapolis, MN (US)

( * ) Notice: Subject to any disclaimer, the term of this patent is extended or adjusted under 35 U.S.C. 154(b) by 517 days.

(21) Appl. No.: 12/423,425

(22) Filed: Apr. 14, 2009

(65) Prior Publication Data

US 2009/0259303 A1 Oct. 15, 2009

Related U.S. Application Data

(60) Provisional application No. 61/044,737, filed on Apr. 14, 2008.

(51) Int. Cl.
*A61F 2/24* (2006.01)

(52) U.S. Cl.
USPC ........................................... 623/2.11

(58) Field of Classification Search
USPC ........................................... 623/2.11
See application file for complete search history.

(56) References Cited

U.S. PATENT DOCUMENTS

| | | | |
|---|---|---|---|
| 3,570,014 A | 3/1971 | Hancock | |
| 3,714,671 A | 2/1973 | Edwards et al. | |
| 4,035,849 A | 7/1977 | Angell et al. | |
| 4,185,636 A | 1/1980 | Gabbay et al. | |
| 4,211,325 A | 7/1980 | Wright | |
| 4,494,253 A | 1/1985 | Bicer | |
| 4,585,453 A | 4/1986 | Martin et al. | |
| 4,605,407 A | 8/1986 | Black et al. | |
| 4,655,218 A | 4/1987 | Kulik et al. | |
| 4,679,556 A | 7/1987 | Lubock et al. | |
| 4,683,883 A | 8/1987 | Martin | |
| 4,801,015 A | 1/1989 | Lubock et al. | |
| 4,865,600 A | 9/1989 | Carpentier et al. | |
| 5,061,278 A | 10/1991 | Bicer | |
| 5,089,015 A | 2/1992 | Ross | |
| 5,236,450 A | 8/1993 | Scott | |
| 5,336,258 A | 8/1994 | Quintero et al. | |
| 5,476,510 A | 12/1995 | Eberhardt et al. | |
| 5,571,174 A | 11/1996 | Love et al. | |
| 5,716,401 A | 2/1998 | Eberhardt et al. | |
| 5,728,153 A | 3/1998 | Menkis et al. | |
| 5,800,531 A * | 9/1998 | Cosgrove et al. | 623/2.11 |
| 5,814,099 A | 9/1998 | Bicer | |
| 6,197,053 B1 * | 3/2001 | Cosgrove et al. | 623/2.11 |
| 6,678,962 B1 * | 1/2004 | Love et al. | 33/512 |
| 6,883,522 B2 | 4/2005 | Spence et al. | |
| 6,951,571 B1 | 10/2005 | Srivastava | |
| 7,410,499 B2 | 8/2008 | Bicer | |
| 7,670,370 B2 * | 3/2010 | Hill et al. | 623/2.11 |
| 2002/0133226 A1 * | 9/2002 | Marquez et al. | 623/2.11 |
| 2006/0287718 A1 | 12/2006 | Bicer | |
| 2007/0219629 A1 | 9/2007 | Bokros et al. | |
| 2007/0244551 A1 * | 10/2007 | Stobie | 623/2.1 |
| 2008/0249620 A1 | 10/2008 | Bicer | |

* cited by examiner

*Primary Examiner* — Melanie Tyson
*Assistant Examiner* — Son Dang

(57) ABSTRACT

An implant holder for removably retaining an implant during an implantation procedure includes a holder device having a frame defining a chamber. The frame may be configured for removable retention of an implant, such as the flexible bioprosthetic heart valve, substantially within the chamber. The removable retention of the implant to the implant holder maintains the implant in an orientation and shape suitable for implantation.

9 Claims, 4 Drawing Sheets

TOOL FOR IMPLANTATION OF REPLACEMENT HEART VALVE

CROSS-REFERENCE TO RELATED APPLICATIONS

This application claims priority to U.S. Provisional Patent Application Ser. No. 61/044,737, filed on Apr. 14, 2008 and entitled "Tool for Implantation of Replacement Heart Valve", the content of which being incorporated herein in its entirety.

FIELD OF THE INVENTION

The present invention relates to devices for implant installation generally, and more particularly to a holder device for use in connection with implantation of replacement heart valves.

BACKGROUND OF THE INVENTION

In some individuals, one or more heart valves may not function normally, typically as a result of disease-induced valve damage, degeneration, or a congenital defect. Valve dysfunction can include valve regurgitation, which can be a life-threatening condition. One method for treating valve dysfunction is valve replacement with one of a variety of replacement valve types. Such replacement heart valves may be relatively rigid or may be flexible, and may be generally categorized into one of two primary classes of replacement heart valves. The first class includes valves commonly referred to as a mechanical prostheses, which typically have one or more relatively rigid leaflets formed of a stiff biocompatible material and/or which include commisures that are self-supporting, and do not need to be affixed to an adjacent structure. Mechanical prostheses are generally formed of artificial materials and rigidities which may be easily handled during surgery, but are more prone to thrombogenesis, and therefore typically require prolonged anti-coagulation therapy.

The second class of replacement heart valves is bioprosthetic or biologic valves, which are typically flexible and may be made of a biological material. This category includes valves harvested from human cadavers (allografts or homografts) or animal tissue (xenografts). More recently, however, flexible replacement valves made of synthetic biologically compatible materials have been developed as substitutes for such natural tissues. Bioprosthetic valves typically do not require lifelong anti-coagulation therapy, as such materials do not often lead to clot formation.

Flexible replacement heart valves, such as flexible bioprosthetic valves may be stented or unstented. A stented valve includes a frame for configurationally supporting the replacement valve, and particularly its commisures, at least in the implantation procedure. Such frames may be permanently or removably secured to the replacement valve. Unstented replacement valves do not include commisure support members to configurationally maintain the replacement valves during implantation, and potentially further in permanent use. The frames may take the form of a wire or other metal or plastic framework which supports the flexible valve material. While stented valves provide a relatively stable and self-supporting structure to facilitate proper implantation and alignment of the commisures, the stent frames can result in narrowing of the valve orifice, and can also cause significant stresses on the commisures during valvular operation. Such stresses can lead to valve degradation and dysfunction.

Unstented valves do not have the drawbacks described above with respect to stented valves. However, unstented valves do not have commisure support, such that implantation of the valve requires a more exacting surgical procedure to properly orient the annulus and commisures at the implantation site. In particular, the surgeon must secure each individual commisure in a precise and correct orientation in order to allow the replacement valve to properly function. Due to the flexible structure of the bioprosthetic valves, such placement and securement is difficult.

In an aortic replacement valve, for example, the commisures must be substantially equally spaced at about 120° apart both at their upper and lower ends. Moreover, the commisures should be substantially perpendicular with respect to the annulus plane. Few devices are currently available to aid the surgeon in correctly orienting the replacement valves in the implantation procedure. In particular, devices are not currently available for maintaining the replacement bioprosthetic valve in a correct orientation and shape while the surgeon secures such replacement valve in an appropriate coronary sinus.

It is therefore a principal object of the present invention to provide an implant holder device which maintains an implant, such as an unstented bioprosthetic heart valve, in a correct orientation and shape during the implantation procedure.

It is a further object of the present invention to provide an implant holder which operably retains the implant in a correct implantation orientation and shape while disposed externally to the implant.

It is a still further object of the present invention to provide an implant holder which enables full installation of the implant while the holder remains secured to the implant.

SUMMARY OF THE INVENTION

By means of the present invention, an implant, such as a replacement heart valve, may be supported in an implantation orientation and shape during the surgical implantation procedure. The implant holder of the present invention is configured to removably retain a flexible implant in an appropriate shape, thereby simplifying the surgical procedure. Specifically, the surgeon, with the use of the implant holder of the present invention, may directly secure the implant in place at the surgical site without having to simultaneously manage the shape and orientation of the implant itself. Such a utility greatly facilitates the surgical implantation procedure.

In one embodiment, the implant holder of the present invention includes a monolithic body defining an axis, and includes a hub and a plurality of circumaxially spaced support struts together defining a chamber. Each of the support struts may be connected to the hub by one or more bridge members, and the support struts each include an annulus support portion and a commisure support portion. The commisure support portion extends between and connects the annulus support portion and the bridge member, with the annulus support members of the plurality of support struts together substantially defining a first circumference about and substantially perpendicular to the axis. Circumaxially adjacent ones of the support struts define gaps between adjacent commisure support portions thereof, wherein the gaps are substantially equally circumaxially spaced about the axis.

In another embodiment, a monolithic holder device, in combination with a flexible bioprosthetic heart valve, includes a frame defining a chamber. The frame may be configured for removable retention of the heart valve substantially within the chamber, and in an orientation and shape suitable for implantation.

In another embodiment, a method for implanting a replacement heart valve into a coronary sinus includes providing a monolithic holder device having a hub and a plurality of circumaxially spaced support struts together defining a chamber. Each of the support struts are connected to the hub by one or more bridge members, and the support struts each include an annulus support portion and a commisure support portion. The annulus support members of the plurality of support struts together substantially define a first circumference about and substantially perpendicular to the axis, and circumaxially adjacent ones of the support struts define gaps between adjacent commisure support portions thereof. The gaps are substantially equally circumaxially spaced about the axis. The replacement heart valve is then positioned in the chamber such that a suture cuff of the replacement heart valve extends about the first circumference, a commisure of the replacement heart valve extends into or through a gap, and commisure tabs coupled to respective commisures of the replacement heart valve are disposed radially outwardly of the support struts. A first suture is affixed to the commisure tabs, wherein the first suture connects the commisure tabs to one another. The first suture is then suspended upon the bridge members. The holder device is then located at the coronary sinus, and the suture cuff and the commisure tabs are sutured to a wall of the coronary sinus. The first suture is then severed, thereby releasing the replacement heart valve from the holder device.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various embodiments of the invention. Other embodiments and aspects of the invention are recognized as being within the grasp of those having ordinary skill in the art.

Figure 1:
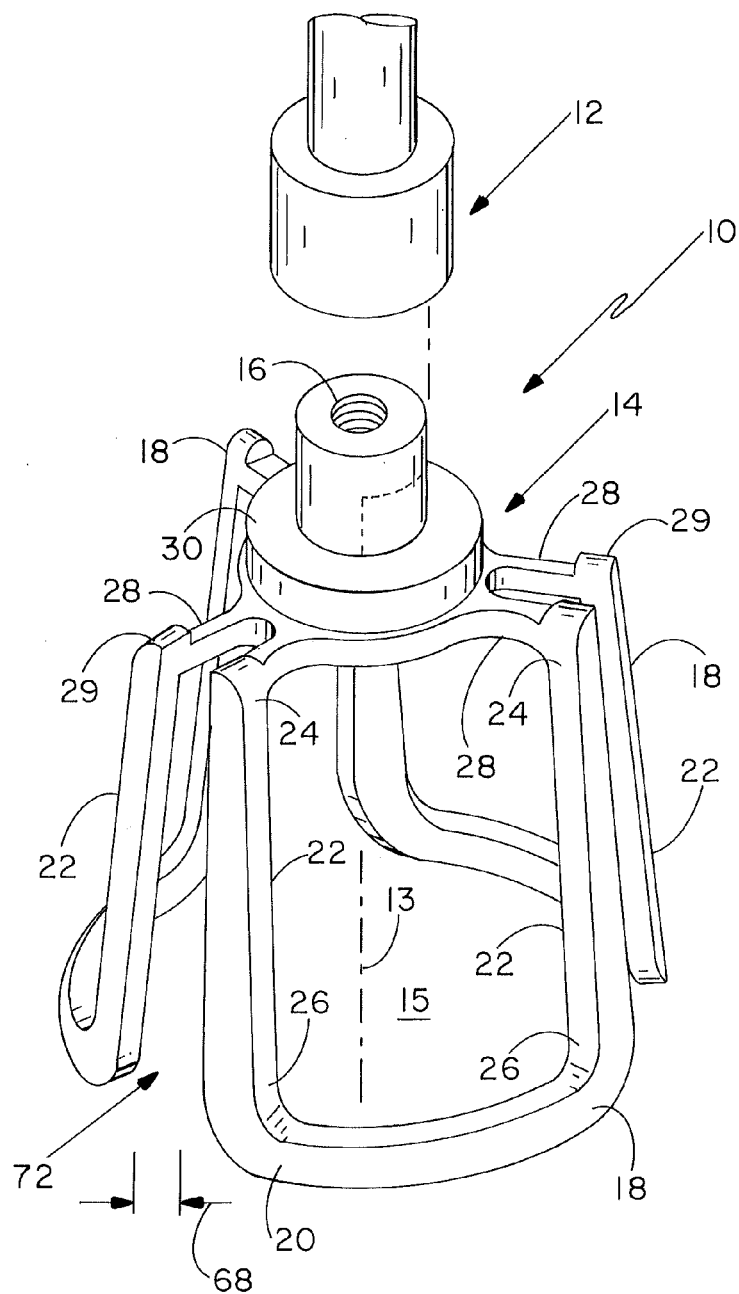
FIG. 1 is a perspective view of an implant holder apparatus of the present invention.

An implant holder 10 of the present invention is illustrated in FIG. 1. implant holder 10 may include an elongate handle 12 which may be used to deploy holder frame 14 to the target surgical site. Handle 12 may be secured to holder frame 14, such as at screw fitting 16 of holder frame 14. It is contemplated that implant holder 10 may be utilized in connection with various implantable bodies, and may be particularly adapted for use in connection with replacement heart valves. The embodiment illustrated in FIG. 1 may be most applicable for use in connection with the implantation of replacement aortic heart valves, and most particularly stentless aortic heart valves. In some cases, such replacement valves may be bioprosthetic, or tissue valves, which may be an allograft, homograft, or xenograft.

As illustrated in FIG. 1, holder frame 14 may be a single-piece monolithic body including a plurality of support struts 18 integrally formed therewith. In one embodiment, holder frame 14 may include three support struts 18 substantially equally spaced about central longitudinal axis 13 of holder 10 to define a chamber 15 substantially bounded by hub 30, bridge members 28, and support struts 18. Such an embodiment may be particularly useful in connection with aortic or other tricuspid heart valves. Fewer or greater numbers of support struts 18, however, are also contemplated as being useful in various applications of the present invention.

In the embodiment illustrated in FIG. 1, support struts 18 are substantially u-shaped, and include an annulus support portion 20 circumaxially disposed about central axis 13, and further disposed substantially along a plane perpendicular to central axis 13. Support struts 18 further include commisure support portions 22 extending generally upwardly from annulus support portion 20. Commisure support portions 22 may be substantially perpendicular to annulus support portion 20, and may be angularly oriented with respect to central axis 13 such that upper ends 24 are more proximate to central axis 13 than lower ends 26 of commisure support portions 22. In this arrangement, support struts 18, in combination, form a substantially frusto-conical configuration for holder frame 14, with annulus support portions 20 collectively defining a relatively larger circumference 64 than an imaginary circumference perpendicularly arranged about axis 13 at upper ends 24 of commisure support portions 22.

In some embodiments, upper ends 24 of commisure support portions 22 may be connected to hub 30 through bridge members 28, or may instead be directly connected to hub 30 in the absence of bridge members 28. In the illustrated embodiment, support struts 18 are integrally formed with hub 30 through bridge members 28, such that holder frame 14 is a single, monolithic body. Multi-piece embodiments that accomplish the functional goals of holder frame 14 are also contemplated as being within the scope of the present invention.

A particular aspect of the present invention is the individual and combined configurations of support struts 18. In particular, support struts 18 are specifically arranged and configured to enable retention of an implant, such as a replacement heart valve, in a precise and correct orientation and shape for implantation at the surgical site. For example, annulus support portions 20 are configured and arranged to support a replacement heart valve annulus in a substantially planar circular configuration oriented substantially perpendicular to central axis 13. Moreover, commisure support portions 22 are arranged and configured to retain respective commisures of the replacement heart valves in substantially equally circumaxially spaced-apart arrangement, and substantially equally radially spaced from central axis 13. In this manner, the replacement heart valve commisures are substantially erect, substantially equally spaced-apart, and positioned in a non-skewed orientation with respect to the replacement valve annulus, while the replacement valve is located at chamber 15.

Figure 2:
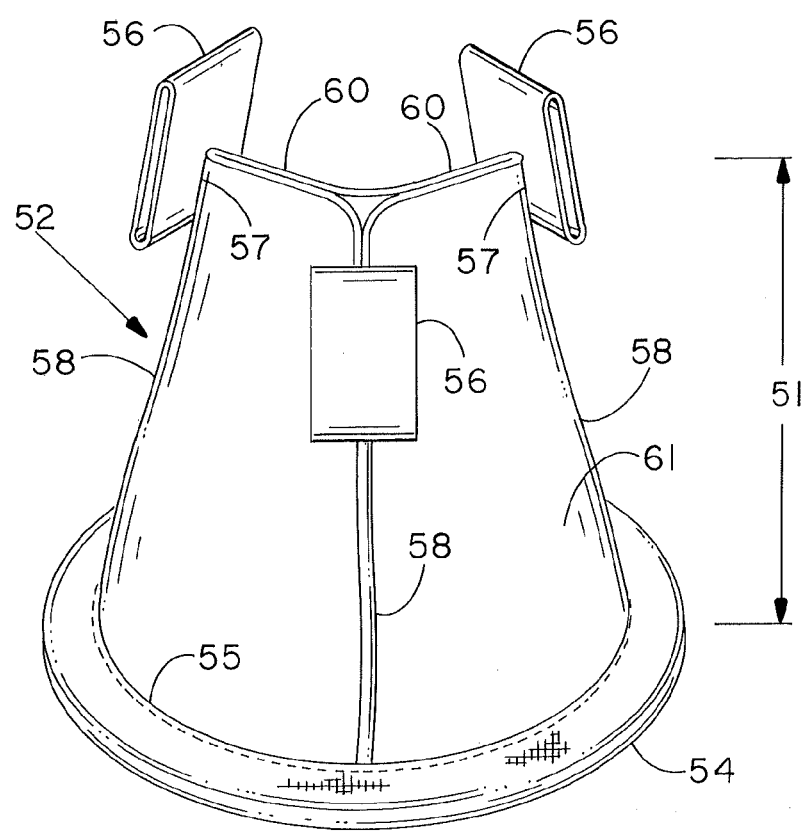
FIG. 2 is a perspective view of an example implant useful in connection with the implant holder of the present invention.

A stentless replacement aortic valve 52 which may be operably secured to holder frame 14 of heart valve holder 10 is illustrated in FIG. 2. Typically, and in the embodiment illustrated in FIG. 2, replacement valve 52 includes a sewing cuff 54 sutured to the valve annulus 55 for use by the surgeon in securing valve annulus 55 to the aortic root. Replacement valve 52, as a replacement aortic valve, includes three commisures 58 substantially equally circumaxially spaced about valve wall 61. In some embodiments, commisure tabs 56 are sutured to respective upper portions 57 of each commisure 58 as a means for facilitating the securement of the replacement valve commisures 58 to the surgical site, such as the aortic root. Commisure tabs 56 are typically made of a fabric or other biocompatible material, and act as a loci for sutures securing commisure tabs 56 to the target fixation location for each valve commisure 58. In the embodiment illustrated in FIG. 2, three commisure tabs 56 are provided, one for each commisure 58 in a replacement aortic heart valve.

Figure 3:
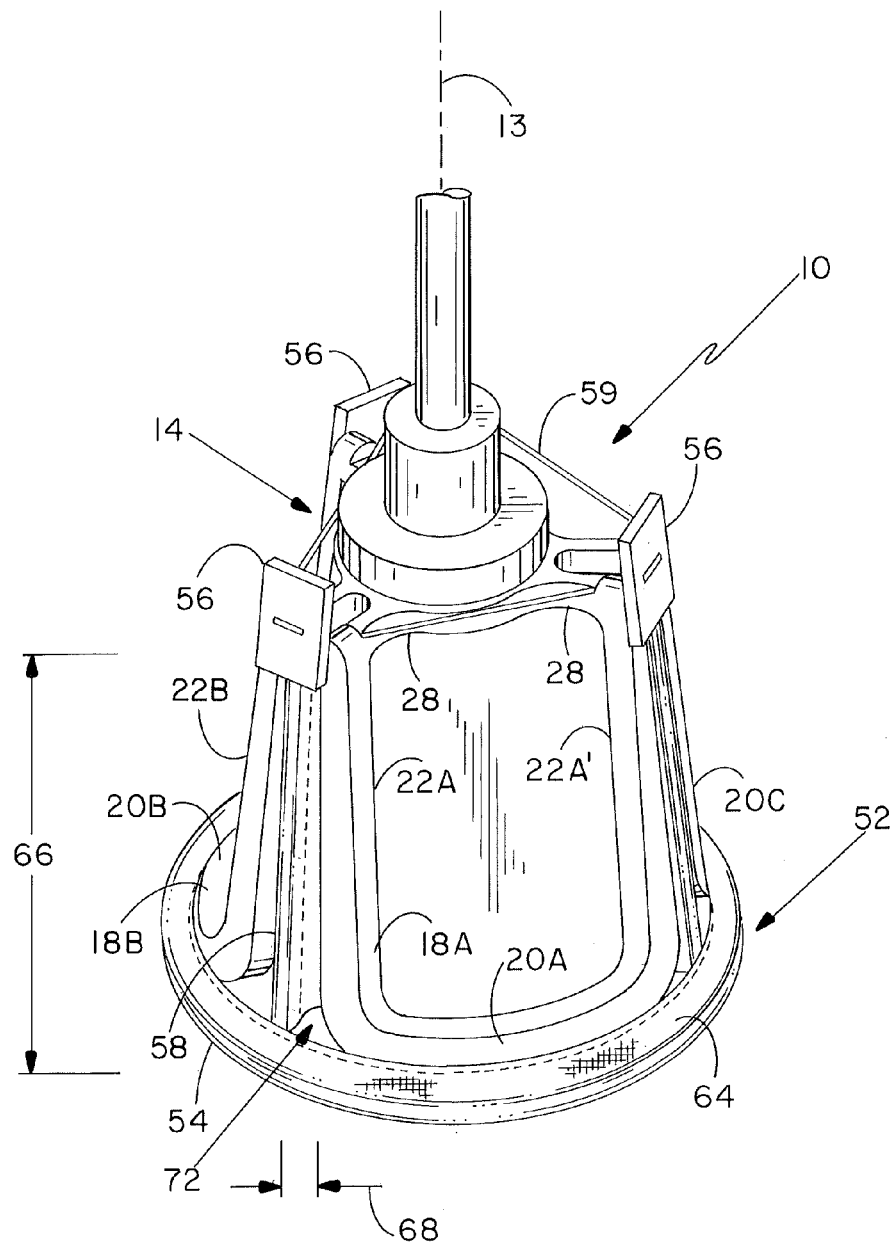
FIG. 3 is a schematic perspective view of the implant of FIG. 2 removably secured to the implant holder apparatus of FIG. 1.

With reference to FIG. 3, a stentless replacement aortic valve 52 is illustrated in a secured condition in chamber 15 of holder frame 14 of implant holder 10. Annulus support portions 20A, 20B, 20C, in combination, support and retain sewing cuff 54 (and valve annulus 55) in a substantially circular configuration along a plane substantially perpendicular to central axis 13. Moreover, holder frame 14 is configured such that sewing cuff 54 is operably disposed radially outwardly of annulus support portions 20A, 20B, 20C with respect to central axis 13, such that a surgeon has direct access to sewing cuff 54 during the implantation procedure while replacement valve 52 is retained within chamber 15 of holder frame 14. Accordingly, the surgeon is able to secure replacement valve annulus 55 to, for example, the aortic root while the replacement valve 52 is maintained in a correct configuration and orientation without requiring the surgeon to separately manipulate and maintain such configuration and orientation. Through the use of implant holder 10, therefore, the surgeon can focus on securing suture cuff 54 at the appropriate location without simultaneously needing to manipulate and maintain the correct orientation and configuration of the replacement valve 52. In order to effectuate this characteristic, the circumference 64 collectively defined by annulus support portions 20A, 20B, 20C is preferably appropriately sized in relation to the replacement valve annulus 55.

In some embodiments, support struts 18 are configured such that a circumference 64 defined by annulus support portions 20A, 20B, 20C is substantially equal in diameter to an inner diameter dimension of an inner circumference of sewing cuff 54, which is also substantially equal to a diameter of replacement valve annulus 55. In such a manner, an inner circumference of sewing cuff 54 is operably placed in contact with annulus support portions 20A, 20B, 20C to thereby removably retain sewing cuff 54 in an appropriate configuration and orientation at holder frame 14.

A further aspect of holder frame 14 is the predetermined height dimension 66 of commisure support portions 22, which height dimension 66 may be substantially equal to a height dimension 51 of the replacement heart valve, as measured from annulus 55 to a top end 60 of each commisure 58. Commisure support portions 22, therefore, may be configured with a height dimension 66 which approximates height dimensions 51 of corresponding replacement valves so that the respective commisures 58 may be suspendedly and removably retained at holder frame 14 in a substantially fully erect orientation and shape. The dimension of circumference 64 and height dimension 66 of holder frame 14 may therefore be sized in accordance with the respective replacement valves being utilized.

A further aspect of holder frame 14 of the present invention is the relative circumaxial spacing of adjacent support struts 18, and particularly the relative circumaxial spacing between commisure support portions 22 of adjacent support struts 18. As illustrated in FIG. 3, support strut 18A includes first and second commisure support portions 22A, 22A', while second support strut 18B includes first and second commisure support portions 22B, 22B'. Adjacent commisure support portions 22A, 22B may be circumaxially spaced apart from one another by at least a spacing dimension 68 to form slot 72 therebetween. Slot 72 may be configured to allow a commisure 58 of replacement valve 52 to extend within and/or through slot 72. In such a manner, slot 72, defined between respective circumaxially spaced apart support struts 18, enable holder frame 14 to fit over and about replacement heart valve 52, while suture cuff 54 and commisure tabs 56 extend radially outwardly beyond an outer perimeter of holder frame 14 to enable direct access thereto by a surgeon while replacement valve 52 is engaged with holder frame 14 at chamber 15.

In order to suspendedly retain replacement valve 52 at holder frame 14, one or more sutures 59 secure commisure tabs 56 to one another at respective top ends 24 of commisure support portions 22. In the embodiment illustrated in FIG. 2, suture 59 secures commisure tabs 56 and is suspended upon respective bridge members 28. Because commisure tabs 56 are separately secured to commisures 58 of replacement valve 52, suture 59 operably suspends replacement valve 52 at holder frame 14, and particularly at bridge members 28 of holder frame 14, due to the operable suspension at suture 59 by bridge members 28. In this fashion, removable securement of replacement valve 52 to holder frame 14 is made at several points of engagement. First, suture cuff 54 may be placed into contact with respective annulus support portions 20 to maintain a substantially annular configuration therefor. Second, commisure tabs 56 may be drawn against an outer surface of respective commisure support portions 22 through tension derived at suture 59. Further, suture 59, which couples commisure tabs 56 to one another, may be brought into bearing contact against commisure support portions 22 and/or bridge members 28. The combination of such retention points effectively removably secures replacement valve 52 to holder frame 14 in a desired orientation and shape.

In some embodiments, upper ends 24 of commisure support portions 22 may include an upwardly-extending protrusion 29 which extends substantially axially upwardly beyond bridge members 28. Protrusions 29 may extend between about 1 and about 5 mm above bridge members 28, and can thereby act to assist in retaining suture 59 at holder frame 14.

Holder frame 14 may be fabricated from a variety of materials which are preferably sterilizable. In some embodiments, a non-elastomeric material such as Delrin™, may be preferred in the manufacture of holder frame 14. Since heart valve holder 10 is intended to be only temporarily utilized in a valve implantation procedure, valve holder 10 need not be fabricated of a completely biocompatible material, but rather of one or more materials that may be used temporarily within the patient's body. In some embodiments, holder frame 14 may be fabricated from a metal, such as reshapable materials including nitinol.

Figure 4:
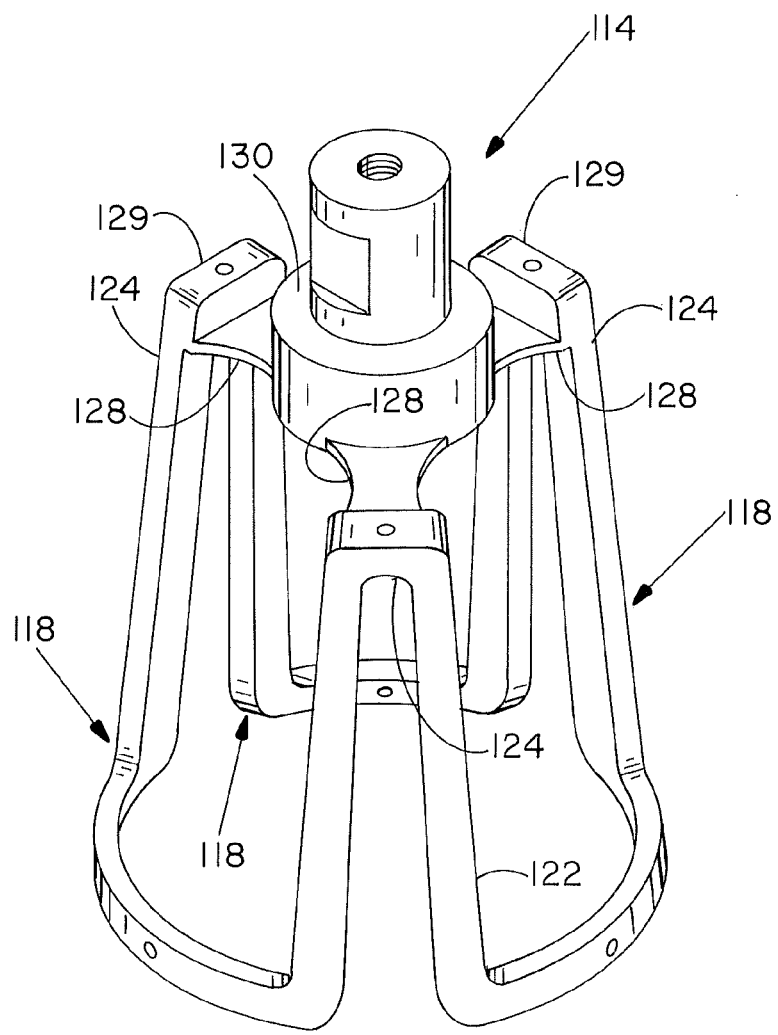
FIG. 4 is a perspective view of an implant holder device of the present invention.

Another embodiment of the invention is illustrated in FIG. 4, wherein holder frame 114 includes a plurality of support struts 118 integrally formed therewith. Holder frame 114 is similar to holder frame 14 described hereinabove, with the primary exception being bridge portions 128 each being a single body extending from hub 130 to respective upper ends 124 of commisure support portions 122. Moreover, respective commisure support portions 122 of adjacent support struts 118 are connected at respective upper ends 124 thereof. Upwardly extending protrusions 129 are also provided at holder frame 114. It is contemplated that holder frame 114 operates to removably retain a replacement valve, such as aortic replacement valve 52, during an implantation procedure for replacement valve 52 at the surgical site.

A replacement valve implantation procedure facilitated by implant holders 10, 110 of the present invention is now described. Once the surgeon has excised the diseased valve, the recipient native aortic root is sized, and an unstented bioprosthetic valve of the appropriate size is selected for implantation. The replacement valve, with its suture cuff 54, and commisure tabs 56, is removably secured to holder frame 14 of implant holder 10 as described above, wherein commisures 58 of replacement valve 52 extend into slot 72, and commisure tabs 56 are positioned radially outwardly of commisure support portions 22. One or more sutures 59 are then secured to and between commisure tabs 56 to thereby couple the commisure tabs 56 to another. Commisure tabs 56 are adjacent to upper ends 24 of commisure support portions 22, and in facing relationship with respective outer surfaces of commisure support portions 22, which suture 59 is operably suspended upon bridge members 28. The secured unstented replacement valve is then brought into position inside the recipient native aortic root, and sutures are placed through the unstented valve annulus/suture cuff 54, and through the recipient native aortic annulus. Sutures are then placed through commisure tabs 56 and through the recipient native aortic annulus in order to permanently affix replacement valve 52 thereat. Suture 59 is then severed, such that holder frame 14 may be removed from engagement with replacement valve 52. Implant holder 10 is then removed from the patient leaving the permanently installed replacement valve 52 in correct configuration and orientation within the native aortic root.

EXAMPLE

The following sets forth one example embodiment of a holder frame 14 of the present invention. It is to be understood, however, that the following dimensions are merely exemplary of a single embodiment of the present invention, and that Applicants contemplate a variety of embodiments, including various dimensions and relative dimensions of the portions of holder frame 14. Specifically, Applicants contemplate that holder frame 14 may be variously dimensioned so as to appropriately accommodate replacement valves or other implants of various sizes.

The following table sets forth example dimensions for portions of holder frame 14 described above:

| Holder Frame Portion | Dimensions (mm) |
| --- | --- |
| Circumference 64 | 81.6 (arcuate) |
| Annulus Support Portions 20 | 23.0 (arcuate) |
| Commisure Support Portions 22 | 19.5 (height) |
| Protrusions 29 | 2.0 (height) |
| Slot 72 | 4.2 (min. width) |
| Hub 30 | 6.4 (diameter) |

The invention has been described herein in considerable detail in order to provide those skilled in the art with the information needed to apply the novel principles and to construct and use embodiments of the invention as required. However, it is to be understood that the invention can be carried out by specifically different methods/devices and that various modifications can be accomplished without departing from the scope of the invention itself.

What is claimed is:

1. An implant holder for removably retaining an implant during an implantation procedure, said implant holder comprising:
 a monolithic body defining an axis, said monolithic body having:
 (a) a hub; and
 (b) a plurality of circumaxially spaced support struts together defining a chamber, each of said support struts being connected to said hub by one or more bridge members, said support struts each including an annulus support portion, a first commisure support portion and a second commisure support portion, said commisure support portions extending between and connecting said annulus support portion and said bridge member, with said annulus support members of said plurality of said support struts together substantially defining a first circumference about and substantially perpendicular to said axis, and wherein circumaxially adjacent ones of said support struts define gaps between adjacent commisure support portions thereof, said gaps being substantially equally circumaxially spaced about said axis; and
 wherein said first and second commisure support portions of each support strut are circumaxially spaced from one another, and further wherein said first and second commisure support portions of each support strut are circumaxially spaced from said first and second commisure support portions of remaining ones of said support struts;
 and further wherein a circumaxial spacing between said first and second commisure support portions of each support strut is greater than a circumaxial spacing between circumaxially adjacent ones of said annulus support portions.

2. The implant holder of claim 1, wherein said commisure support portions are substantially perpendicular to said annulus support portion.

3. The implant holder of claim 1, wherein said annulus support portion forms an arcuate segment of said first circumference.

4. The implant holder of claim 1, wherein said one or more bridge members extend radially outwardly from said hub.

5. The implant holder of claim 1, wherein said gaps are circumaxially spaced by about 120° about said axis.

6. The implant holder as in claim 1 wherein said gaps are configured to receive a commisure of a replacement bioprosthetic heart valve therein.

7. An implant holder as in claim 1 wherein said first circumference is specifically sized to be substantially equal to a circumferential dimension of an annulus of a replacement bioprosthetic heart valve.

8. An implant holder as in claim 7 wherein said gaps have a width dimension between adjacent commisure support portions, said width dimension being about 4 mm.

9. An implant holder as in claim 1, wherein said first and second commisure support portions of each support strut are circumaxially spaced from one another, and further wherein said first and second commisure support portions of each support strut are circumaxially spaced from the first and second commisure support portions of the other support struts.

* * * * *